United States Patent
Aeschlimann et al.

(10) Patent No.: US 8,992,507 B2
(45) Date of Patent: Mar. 31, 2015

(54) BAYONET LUER LOCK CONNECTION FOR AN INSULIN PUMP

(75) Inventors: Reto Aeschlimann, Aefligen (CH); Michael Weibel, Alchenfluh (CH)

(73) Assignee: Roche Diagnostics International AG, Rotkreuz (CH)

( * ) Notice: Subject to any disclaimer, the term of this patent is extended or adjusted under 35 U.S.C. 154(b) by 915 days.

(21) Appl. No.: 12/031,503

(22) Filed: Feb. 14, 2008

(65) Prior Publication Data
US 2008/0200900 A1 Aug. 21, 2008

(30) Foreign Application Priority Data
Feb. 15, 2007 (EP) .................................... 07102503

(51) Int. Cl.
A61M 25/16 (2006.01)
F16L 37/107 (2006.01)
A61M 39/10 (2006.01)

(52) U.S. Cl.
CPC .......... *F16L 37/107* (2013.01); *A61M 39/1011* (2013.01); *A61M 2039/1033* (2013.01); *A61M 2039/1077* (2013.01)
USPC .......................................... 604/533; 604/523

(58) Field of Classification Search
USPC ......... 604/240, 241, 242, 243, 246, 533, 534, 604/535, 536, 538, 905
See application file for complete search history.

(56) References Cited

U.S. PATENT DOCUMENTS

| 4,452,473 | A | | 6/1984 | Ruschke | |
|---|---|---|---|---|---|
| 5,209,740 | A | * | 5/1993 | Bryant et al. | 604/243 |
| 5,250,037 | A | * | 10/1993 | Bitdinger | 604/192 |
| 5,456,676 | A | * | 10/1995 | Nelson et al. | 604/533 |
| 5,492,147 | A | * | 2/1996 | Challender et al. | 137/614.05 |
| 5,591,143 | A | * | 1/1997 | Trombley et al. | 604/534 |
| 5,762,646 | A | * | 6/1998 | Cotter | 604/410 |
| 5,830,195 | A | * | 11/1998 | Peters et al. | 604/533 |
| 5,848,997 | A | * | 12/1998 | Erskine et al. | 604/533 |
| 7,080,672 | B2 | * | 7/2006 | Fournie et al. | 141/383 |
| 2006/0033334 | A1 | | 2/2006 | Weber et al. | |
| 2012/0271244 | A1 | * | 10/2012 | Simpson et al. | 604/236 |
| 2013/0310807 | A1 | * | 11/2013 | Adair et al. | 604/533 |

FOREIGN PATENT DOCUMENTS

| DE | 202004012714 | 11/2004 |
|---|---|---|
| EP | 0028198 | 5/1981 |
| FR | 2881503 | 8/2006 |

* cited by examiner

*Primary Examiner* — Kami A Bosworth
*Assistant Examiner* — Imani Hayman
(74) *Attorney, Agent, or Firm* — Dinsmore & Shohl LLP

(57) ABSTRACT

A connection including a first closure component including a first adapter and a fitting element which is able to move relative to the first adapter and an elastic or resilient element which couples the first adapter to the fitting element and/or is disposed between them.

12 Claims, 2 Drawing Sheets

BAYONET LUER LOCK CONNECTION FOR AN INSULIN PUMP

CROSS REFERENCE TO RELATED APPLICATION(S)

Figure 1:
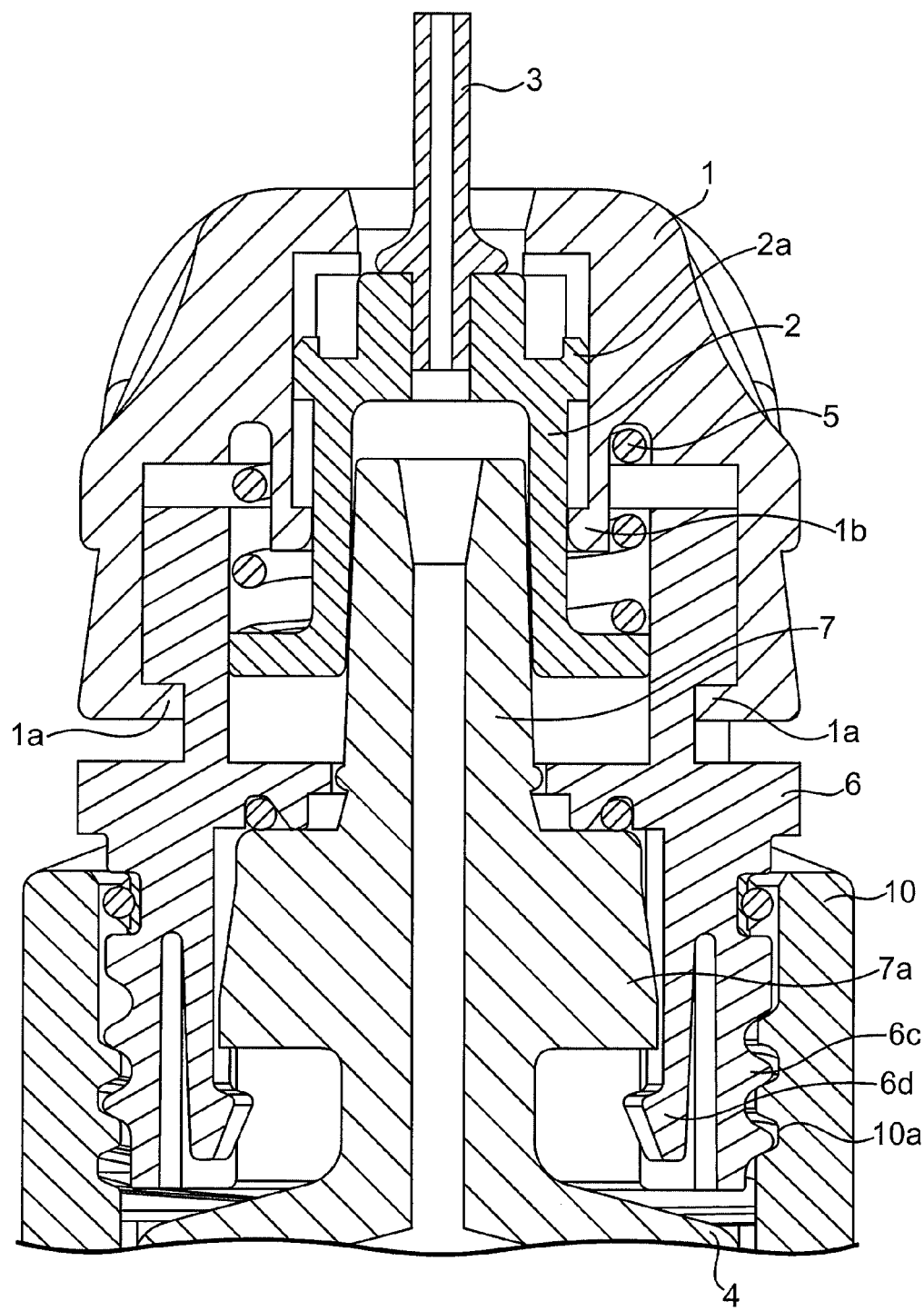

This application claims priority to European Patent Application No. 07 102 503.5-1526, filed Feb. 15, 2007, which is hereby incorporated herein by reference in its entirety.

BACKGROUND

The present invention relates to devices for infusing, injecting, dispensing or delivering a substance, and to methods of making and using such devices. More particularly, it relates to a closure component and a closure for establishing a connection, in particular a fluid connection, to connect a pump or ampoule to a catheter or infusion set, for example.

It is common practice to use a known luer connection to establish a connection between a pump or ampoule and a catheter or infusion set. Typically, a snap-on connection is established between a first and a second connector component, namely a so-called luer male and a so-called luer female, using such a luer connection.

This being the case, the luer female fitting is fitted with the co-operating luer male by a force applied by a user. This can result in an improperly sealed connection if too low a force is applied. However, if the user presses the luer female too firmly onto the luer male, it may be difficult to release the connection. A connection established with too strong a force can also cause the luer to split, which can likewise result in an improperly sealed area.

Another known option for establishing a connection is to use what is known as a luer lock, which additionally establishes a positive connection. In the case of a luer lock connection, an extra internal thread is provided on the male connector piece in addition to the known luer connection, in which an external thread of the female connection can locate.

Luer lock connections are generally designed for establishing connections for only a short time. In the case of pumps, however, they may need to be fitted for up to a week and must guarantee a reliable and sealed connection for the entire period.

Luer fittings are known from ISO 594/1 or DIN EN 20 594-1, for example, the teaching of which with respect to the dimensions and design of luer connections is included in this application.

SUMMARY

One object of the present invention is to provide a closure component or connector by which a releasable connection can be reliably obtained which is durable for a long time.

Another object of the present invention is to provide a closure component or a closure by which a releasable connection can be reliably obtained which is durable for a long time.

In one embodiment, the present invention comprises a connection formed by a first closure component and a second closure component, the connection being releaseable, reliable and durable. In some embodiments, the invention encompasses the connection, the first closure component and/or a second closure component complementary to the first closure component.

In one embodiment, the present invention relates to a first closure component for a closure for establishing a connection, in particular a fluid connection, comprising a first adapter and a fitting element which is able to move or slide relative to the first adapter and an elastic or resilient element which couples the first adapter to the fitting element or is disposed between them.

In one embodiment, the present invention comprises a closure for establishing a connection, the closure including a first closure component including a first adapter and a fitting element which is able to move relative to the first adapter and an elastic or resilient element which couples the first adapter to the fitting element and/or is disposed between them.

In one embodiment, the present invention comprises first closure component for a closure intended to establish a connection, in particular a fluid connection, with another second closure component. In one embodiment, the first closure component has a first adapter, holder or bearing, on or in which a deformable, displaceable or slidable fitting element is mounted, for example, a luer female fitting element. In accordance with the present invention, a force acts between the first adapter and the fitting element, e.g., a spring force, which may be achieved using a spring element acting between the adapter and the fitting element or, alternatively, an elastic material connection or an elastomer. This makes it possible for the fitting element or a luer female to pushed out of the first adapter or also inside the adapter in the direction of a mounting element, such as a luer male for example, thereby generating a defined fitting force between the fitting element and the mounting element or the luer female and luer male. Thus, a durably reliable and releasable luer connection can be established, which ensures a defined force predetermined by the spring element irrespective of the force with which a user fits or joins the closure component, in particular the first adapter, thereby producing a reliable luer connection.

In one embodiment, at least one retaining element may be provided on the first adapter, such as one, two or more catch lugs for example. The retaining element(s) may project out from the first adapter, radially inwardly or outwardly. A firm connection can be established with such a retaining element or catch lug, for example a bayonet connection, with an appropriate co-operating element, such as a second adapter, so that the first adapter bearing the luer female can be firmly connected to the second adapter, which may be designed as a pump adapter and, in some embodiments, once an ampoule has been inserted in a pump, can be fitted on an ampoule or pump.

Accordingly, in some embodiments, the luer female fitting and/or alternatively a luer male connector may be biased in the fitting direction by a spring element or an elastomer in a bayonet luer lock adapter which may be attached to an infusion set. When the bayonet luer lock adapter is fitted on a pump adapter and latched to it by means of a bayonet connection due to a rotation, such as a 90° rotation, the two adapters and hence also the components connected to the adapters, namely a pump or ampoule at one end and an infusion set at the other end for example, are firmly connected to one another. The bayonet luer lock adapter is fitted against the spring force acting on the luer female, and the luer female is pushed upwards by the luer male and is therefore pushed onto the luer male with a constant or defined force which can be adjusted by the spring element or an elastomer. The bayonet luer lock adapter is also pushed upwards by the force of the spring and therefore also assumes a defined position.

Alternatively or in addition to the embodiments described above, an elastic or spring element may also or only be provided on the second adapter, in other words between the adapter and the mounting element, in which case the mounting element is may be displaceable or slidable relative to the second adapter.

In some preferred embodiments, like the luer male connector piece, the luer female connector piece has a slightly (in a selected degree) conically tapering shape, in which case the luer male is provided in the form of a cone or a truncated cone and the luer female serving as the complementary piece has a conical recess tapering in the insertion direction. In some preferred embodiments, the pitch of the conical part-pieces is 6%, and reference may be made to the above-mentioned standard, for example ISO 594-1, with regard to the design of luer female and luer male connectors.

In some embodiments, if a 6%-luer is used, i.e. a luer connection in which the pitch of the luer male external face is 6%, a clearance of the luer female of approximately 2 mm in the axial direction may be sufficient to compensate for any manufacturing tolerances of the luer connection.

In some preferred embodiments, the fitting element may be mounted in the first adapter or connected to the first adapter so that it can not fall out of the first adapter or be pushed out by the spring force, for example. The fitting element or luer female may be secured by stop elements, projections or wings pointing radially outwardly, for example, which are guided in grooves of the first adapter, before it can fall down out of the first adapter. An annular element may also be provided on the external face of the fitting element. As the fitting element is being inserted in the first adapter, the projections or stops of the fitting element mentioned by way of example may move past elastic snappers or arms of the first adapter biased radially inwardly, for example, which then snap back into the initial position once the retaining element or elements of the first adapter have moved past them to secure the fitting element or luer female and prevent it from falling out of the first adapter. In addition or as an alternative, the fitting element or luer female may be secured by a top widening or a conically tapering part-piece before it can fall down out of the first adapter. To this end, the first adapter may also have a conically tapering recess or a stop element against which a widening of the fitting element lies when the fitting element is in a maximum permissible position pushed out of or extracted from the adapter. The luer female may also be prevented from falling out by a groove in the bayonet luer lock adapter or a top widening of the luer female, for example, which may be inserted in a funnel-shaped top orifice of the bayonet luer lock adapter. Similarly, the mounting element may also be mounted in a secured arrangement in the second adapter to prevent it from falling out.

In some embodiments, the present invention comprises a second closure component. The second closure component of the fitting or connection which may co-operate with the first closure component described above has a mounting element such as a luer male, on which the fitting element described above, in other words the luer female, can be fitted. A second adapter is also provided, on which the first adapter described above can be fitted, in which case the second adapter may have one or more retaining elements, such as a catch groove in which co-operating retaining elements or catch lugs of the first adapter may engage. The retaining element or elements of the second adapter is or are designed so that the first adapter can be turned by 90° before the catch connection is established once it has been fitted on the second adapter, thereby resulting in a bayonet or bayonet-type closure or connection between the first and second adapter.

In some embodiments, to release the bayonet luer lock adapter from the first adapter, it may be pushed in the direction towards the first adapter to release the bayonet closure latching in the catch groove of the second or pump adapter against the force of the spring element. The bayonet luer lock adapter can then be turned, e.g. by 90°, and removed from the pump adapter.

In some embodiments, the present invention may be used to establish a connection with the first closure component described above as well as a standard luer ampoule or a standard luer fitting.

BRIEF DESCRIPTION OF THE DRAWING(S)

Figure 2:
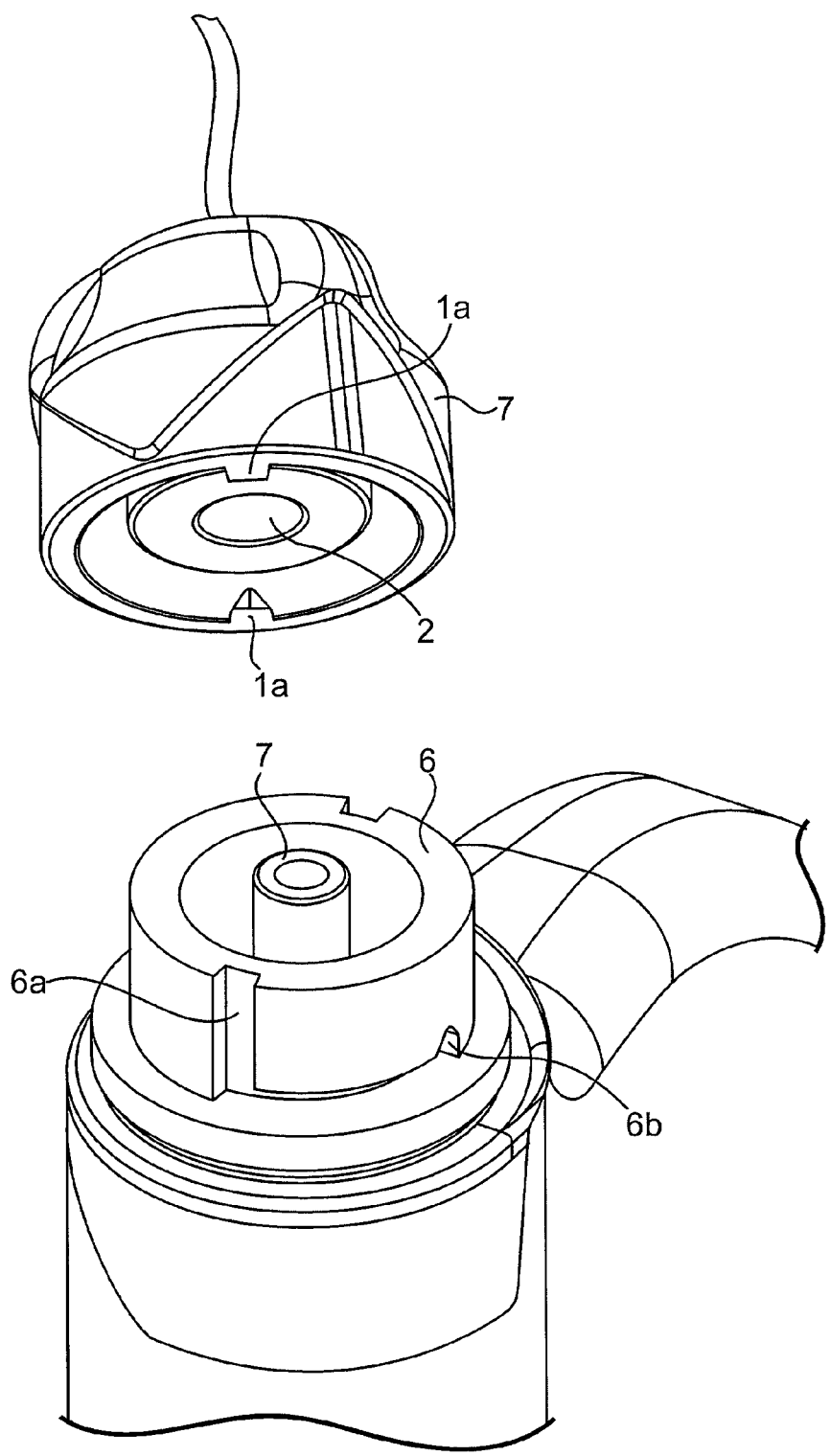

FIG. 1 is a detailed cross-section of a first embodiment of a bayonet luer lock adapter; and FIG. 2 is a perspective view of an embodiment of a bayonet luer lock adapter designed for fitting on a pump.

DETAILED DESCRIPTION

With regard to fastening, mounting, attaching or connecting components or structural features of the present invention, unless specifically described as otherwise, known mechanical fasteners and methods may be used. Other appropriate fastening or attachment methods include adhesives, welding and soldering. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, elastomers, etc.

FIG. 1 is a cross-section illustrating a bayonet luer lock connection with a first adapter 1 in the form of a bayonet luer lock adapter. Disposed in the first adapter 1, which is more or less rotationally symmetrical about the mid-axis of FIG. 1, so that it can slide in the axial direction of the first adapter 1, is a luer female 2 serving as a fitting element. A catheter or hose 3 may be attached, possibly fixedly, to the luer female 2, through which a substance to be dispensed from an ampoule pump or ampoule 4 is transferred to an infusion set, although this is not illustrated.

A spring 5 serving as an elastic or resilient element is provided between the first adapter 1 and the luer female 2, which pushes the luer female 2 away from the first adapter 1, e.g., downwardly in the orientation illustrated in FIG. 1.

The first adapter 1 is fitted on a second or pump adapter 6, which is attached to the ampoule 4 and screwed onto the pump 10. As illustrated in FIG. 2, the pump adapter 6 has a guide groove 6a extending in the axial direction of the pump adapter 6, in which a catch lug 1a of the first adapter 1 pointing radially inwardly can be guided as the first adapter 1 is being fitted on the pump adapter 6. When the first adapter 1 is pushed far enough onto the pump adapter 6 that the catch lug 1a has passed through the entire guide groove 6a in the axial direction, the first adapter 1 can be turned relative to the pump adapter 6, guided by the guide groove 6a extending in the circumferential direction, as a result of which the catch lug 1a of the first adapter 1 guided in the guide groove 6a is pushed so far in the circumferential direction of the pump adapter 6 that the catch lug 1a engages in the catch groove 6b of the pump adapter 6. The catch groove 6b is a cut-out of the guide groove 6a, for example, pointing in the axial direction towards the first adapter 1 provided for guiding the rotating movement in the circumferential direction, and when it is in the position fitted on the pump adapter 6, the first adapter 1 is pushed by the spring 5 away from the pump adapter 6, e.g. upwardly in the orientation illustrated in FIG. 1, so that a catch connection is established between the catch groove 6b and catch lug 1a and a bayonet closure can therefore be produced between the first adapter 1 and the pump adapter 6. The ampoule 4 is held secured in the pump 10 at its bottom end and fixed by the adapter 6 at its top end and is thus prevented from sliding axially.

When the first adapter 1 is fitted on the pump adapter 6 so that the catch lug 1a latches in the catch groove 6b, the luer female 2 coupled with the first adapter 1 via the spring 5 lies on the luer male 7 of the ampoule 4 with a defined pressing force due to the force of the spring 5.

For the purpose of the invention, the pressing force of the luer female 2 on the luer male 7 is therefore not affected by the pressing force of a user merely placing the first adapter 1 on the pump adapter 6 and the above-mentioned problems associated with a luer connection fitted with too low or too high a pressure can therefore be avoided.

As illustrated in FIG. 1, the pump adapter 6 is screwed into a pump 10 in which the ampoule 4 is mounted and has an external thread 6c which locates in an internal thread 10a of an ampoule fitting.

As may be seen from FIG. 1, the luer female 2 has two projections or wings extending radially outwardly or also a circumferentially extending ring 2a which forms a lock to prevent the luer female 2 from falling out of the first adapter. When the luer female 2 is inserted in the first adapter 1, the projections or the ring 2a are pushed past the snappers or arms 1b of the adapter biased radially inwardly and have a rounded region or chamfer on which a front rounded region or chamfer of the projections 2a moves into abutment when the luer female 2 has to be inserted in the first adapter 1, so that the snapper arms 1b are pushed radially outwardly. When the luer female 2 has been pushed far enough into the first adapter 1 for the retaining elements 2a to have moved past the arms 1b, the arms 1b biased radially inwardly resume the initial position illustrated in FIG. 1 and the luer female 2 can therefore be prevented from falling out of the first adapter 1 due to the retaining action of the retaining elements 2a.

The pump adapter 6 has snapper arms 6d biased radially inwardly on its bottom face directed towards the pump 10, which locate behind a projection 7a of the luer male 7 so that the ampoule 4 is locked to prevent it from falling out in the state when the adapter 6 is not screwed into a pump 10.

While embodiments of the present invention have been described with reference to ampoules and/or insulin pumps, it should be appreciated that they may find use in other fields and/or applications, e.g., any of those wherein a reliable, durable, relatively short or long term connection or joint may be desirable or suitable, e.g., in any gas, fluid or liquid handling situation.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A connection comprising:
   a first closure component comprising a first adapter, a fitting element, and a coupling element, wherein the entirety of the fitting element moves relative to the first adapter, and wherein the coupling element is at least one of elastic and resilient and couples the first adapter with the fitting element along with a force that acts between the first adapter and the fitting element, wherein the force allows the fitting element to push out from the first adapter;
   a second closure component comprising a mounting element on which the fitting element of the first closure component can be fitted and a second adapter to which the first adapter of the first closure component can be positively connected, where the force allows the fitting element inside the adapter to push toward the direction of the mounting element to form the connection between the fitting element and the mounting element, wherein the second adapter comprises a guide groove comprising a first part and a second part, wherein the first part extends longitudinally, in an axial direction of the second adapter, and the second part extends longitudinally from the first part, in a circumferential direction with respect to the second adapter, and that ends in a catch groove; and
   wherein the second adapter comprises an external thread to screw into a pump and comprises snapper arms to couple to the pump to prevent the second adapter from uncoupling from the pump; and
   the snapper arms are configured to extend substantially linearly along the outer surface of an ampoule in a direction of a longitudinal axis of the second adapter, the external thread located at a periphery of the second adapter and the snapper arms positioned internal to the external thread in relation to the periphery of the second adapter.

2. The connection according to claim 1, wherein the first adapter is moveable relative to the second adapter in an axial and a circumferential direction.

3. A connection comprising:
   a first closure component for a closure designed to establish a connection, the first closure component comprising a first adapter, a fitting element, and a coupling element, wherein the entirety of the fitting element moves relative to the first adapter, the coupling element is at least one of elastic and resilient and couples the first adapter with the fitting element and a second closure component comprising a mounting element on which the fitting element of the first closure component can be fitted and a second adapter to which the first adapter of the first closure component can be positively connected, wherein the second adapter comprises a guide groove comprising a first part and a second part, wherein the first part extends longitudinally in an axial direction of the second adapter, and the second part extends longitudinally in a circumferential direction of the second adapter;
   wherein the first and second closure components are configured such that upon coupling of the first and second adapters, in each position of the fitting element relative to the mounting element, a substantially unobstructed flow path for passing fluid between the first and second closure components is formed; and
   wherein the second adapter comprises an external thread to screw into a pump and comprises snapper arms to couple to the pump to prevent the second adapter from uncoupling from the pump; and
   the snapper arms are configured to extend substantially linearly along an outer surface of an ampoule in a direction of a longitudinal axis of the second adapter, the external thread located at a periphery of the second adapter and the snapper arms positioned internal to the external thread in relation to the periphery of the second adapter.

4. The connection according to claim 3, wherein the coupling element is disposed between the first adapter and the fitting element.

5. The connection as claimed in claim 3, wherein the fitting element comprises a conical taper.

6. The connection as claimed in claim 3, wherein the fitting element comprises a fitting for at least one of an infusion set, a catheter, a cannula and a hose.

7. The connection as claimed in claim 3, wherein the fitting element comprises a lock structure that prevents the fitting element from falling out of a conically widening or projecting region.

8. The connection according to claim 3, wherein the first adapter comprises at least one retaining element pointing radially inward, and wherein that at least one retaining element comprises at least one such leg.

9. The connection as claimed in claim 4, wherein the coupling element is a spring or elastomer that moves a catch lug axially in relation to the second closure component in a direction toward the coupling end of the luer male and into the catch groove, the catch lug held biased therein.

10. The connection as claimed in claim 3, wherein the guide groove is designed so that the first adapter can be guided in or on the second adapter in axial and circumferential directions.

11. The connection as claimed in claim 3, wherein the guide groove is designed so that the first adapter can be guided in or on the second adapter in the axial direction and then in the circumferential direction.

12. A connection comprising:
a first closure component comprising a first adapter, a fitting element, and a coupling element, wherein the entirety of the fitting element moves relative to the first adapter, and the coupling element is at least one of elastic and resilient, and couples the first adapter with the fitting element along with a force that acts between the first adapter and the fitting element, wherein the force allows the fitting element to push out from the first adapter, and the first adapter comprises a retaining element extending radially inward therefrom; and
a second closure component comprising a mounting element on which the fitting element of the first closure component is fitted and a second adapter to which the first adapter of the first closure component can be positively connected, where the force allows the fitting element inside the first adapter to push toward the direction of the mounting element to form the connection between the fitting element and the mounting element, wherein the second adapter comprises a guide groove comprising a first part and a second part, wherein the first part extends longitudinally in an axial direction of the second adapter, and the second part extends longitudinally in a circumferential direction with respect to the second adapter;
wherein axial movement of the first adapter relative to the second adapter is guided by a sliding movement of the retaining element in the first part of the guide groove, and rotational movement of the first adapter relative to the second adapter is guided by a sliding movement of the retaining element in the second part of the guide groove; and
wherein the second adapter comprises an external thread to screw into a pump and comprises snapper arms to couple to the pump to prevent the second adapter from uncoupling from the pump; and
the snapper arms are configured to extend substantially linearly along the outer surface of an ampoule in a direction of a longitudinal axis of the second adapter, the external thread located at a periphery of the second adapter and the snapper arms positioned internal to the external thread in relation to the periphery of the second adapter.

* * * * *